United States Patent [19]

Altner et al.

[11] Patent Number: 4,715,370
[45] Date of Patent: Dec. 29, 1987

[54] OVERFLOW TRAP FOR ANESTHETICS

[75] Inventors: Ulrich Altner, Bad Segeberg; Wolfgang Falb, Klein Wesenberg; Martin Ryschka, Stockelsdorf; Carl-Friedrich Wallroth, Lübeck, all of Fed. Rep. of Germany

[73] Assignee: Drägerwerk Aktiengesellschaft, Fed. Rep. of Germany

[21] Appl. No.: 940,627

[22] Filed: Dec. 11, 1986

[30] Foreign Application Priority Data

Dec. 14, 1985 [DE] Fed. Rep. of Germany ....... 3544302

[51] Int. Cl.$^4$ .............................................. A61M 15/00
[52] U.S. Cl. .......................... 128/204.13; 128/203.12; 137/592; 261/DIG. 65
[58] Field of Search ...................... 128/203.12, 203.25, 128/204.13; 137/577, 577.5, 590, 590.5, 592; 141/9; 261/DIG. 65

[56] References Cited

U.S. PATENT DOCUMENTS

| 479,594 | 7/1892 | Hildebrandt | 137/592 |
| 509,849 | 11/1893 | Hayes | 128/203.25 X |
| 3,420,232 | 1/1969 | Bickford | 128/203.25 |
| 3,638,676 | 2/1972 | Burch et al. | 137/592 X |
| 4,444,182 | 4/1984 | Gregory | 128/203.25 |
| 4,607,634 | 8/1986 | Clapham | 128/203.25 |

*Primary Examiner*—Mark J. Thronson
*Attorney, Agent, or Firm*—McGlew and Tuttle

[57] ABSTRACT

An overflow trap on a reservoir for liquid anesthetics with at least one inlet conduit for filling and an overflow conduit for overflow which both open at its side wall. The entering of anesthetic liquid from a feed tank through the inlet and the overflow of anesthetic due to shifts or rocking of the liquid level is prevented. For this purpose, the inlet conduit and the overflow conduit are slanted toward the bottom of the reservoir and they have openings close to a wall of the reservoir which is opposite to the inlet and the overflow openings of the conduits.

4 Claims, 1 Drawing Figure

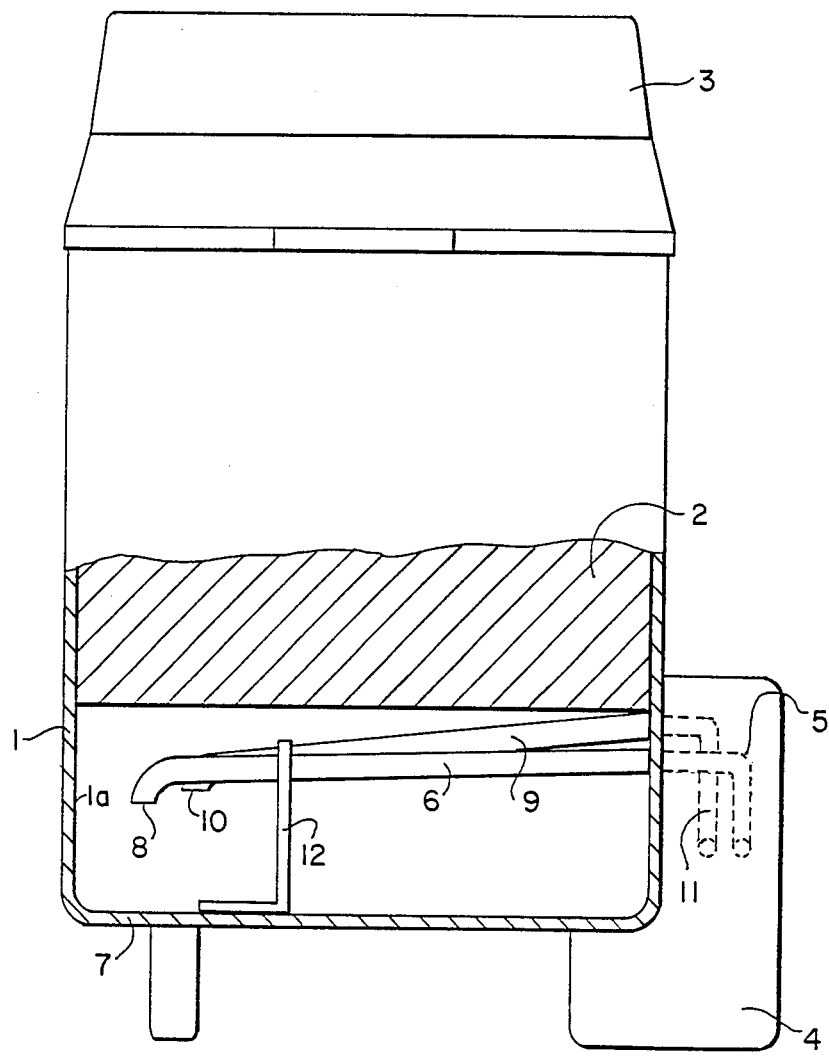

OVERFLOW TRAP FOR ANESTHETICS

FIELD AND BACKGROUND OF THE INVENTION

This invention relates in general to devices for handling anesthetics and in particular to a new and useful overflow trap for a liquid anesthetic reservoir.

The invention relates particularly to an overflow trap on a container for liquid anesthetics, in which at least one inlet for filling and overflow extend with their openings to its side wall.

Liquid anesthetics frequently are fed through an anesthetic vaporizer into the breathing gas of the patient to whom the narcosis is to be administered. A storage container with anesthetic attached to the vaporizer permits a longer use of the vaporizer during a narcosis. The filling of the anesthetic reservoir is taken care of before its use or after a relatively extended operating time of the anesthetic vaporizer. The anesthetic reservoir is equipped with an overflow to prevent excessive filling of the anesthetic reservoir. This type of overflow trap is described in the German operating instructions 5327.09, Feb. '83: "Safety Filling Device for the Vapor 19.1" by the company Drägerwerk AG, Lübeck, Federal Republic of Germany. The anesthetic reservoir of the anesthetic vaporizer is equipped laterally with a filling device to which the filling hose of the anesthetic bottle can be attached via a joining socket.

The filling hose has a coupling unit that can be coupled with the joining socket. The filling channel for the anesthetic and the ventilating channel for the ventilation of the anesthetic bottle during the feeding of the anesthetic into the anesthetic reservoir are located in the coupling unit and the filling hose. When the filling hose is coupled, the filling channel and the ventilating channel extend in the filling equipment and open laterally as an inlet and as a ventilation opening into the anesthetic reservoir. When the anesthetic is transferred from the anesthetic bottle into the anesthetic reservoir, the liquid leaves the inlet, and the air present in the anesthetic reservoir is returned to the anesthetic bottle via the ventilating opening. As a predetermined maximal filling level is reached, the ventilating opening is closed and the filling from the anesthetic bottle is stopped. But in the event that a further filling of the anesthetic reservoir beyond the maximal filling level takes place, due to a failure, e.g. a defective seal in the filling hose, an additional overflow is located on the reservoir, through which the excess anesthetic can drain off.

When a filled anesthetic reservoir is tilted in its position to such an extent that the liquid enters the inlet and the overflow due to a shock, a residual amount of anesthetic liquid cannot be removed from sections of the channel line into the feeding equipment. It flows out either immediately or after the opening of a closure and irritates the persons present in the neighborhood.

SUMMARY OF THE INVENTION

The present invention provides an improved overflow so that an entering of anesthetic liquid into the inlet and the overflow is prevented, even when the liquid level in the anesthetic reservoir is tilted or rocked.

In accordance with the invention the inlet and the overflow, are conducted through respective lengths of pipe slanted toward the bottom of the reservoir, with openings close to the wall of the reservoir opposite the inlet and the overflow.

The advantages obtained with the invention are especially seen in the fact that with small tilts about the vertical axis of the anesthetic reservoir, but particularly with shifts in the liquid level due to shocks, the level of the liquid can enter the free pipe end of the piece of pipe only to a certain length, but is forced, due to the pipe's inclination, to flow back into the anesthetic reservoir. An overflowing of the channel in the filling direction is thereby prevented. The pipe length may extend straight, but bent, spiral or similar configurations can also be used.

The angles of the openings of the pipe lengths prevent a direct entering of liquid splashes deep into the pipe lengths.

Accordingly it is an object of the invention to provide an overflow trap for anesthetics which includes an inlet conduit and an overflow conduit which extends into an anesthetic reservoir tank and which extends downwardly toward the bottom in an arrangement which will prevent back flow through the conduits.

A further object of the invention is to provide an anesthetic container which includes an upper portion containing an anesthetic and a lower portion having inlet and outlet conduit connections extending in from one side to a spaced location from the opposite side and being slanted downwardly and connected at their exteriors to feed tanks for anesthetics in which they are located adjacent the upper portion thereof.

A further object of the invention is to provide an anesthetic overflow for an anesthetic reservoir which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE of the drawings is a partial elevational and sectional view of an anesthetic tank and feed connection constructed in accordance with the invention.

DESCRIPTION OF THE PREFERRED EMBODIMENT

Referring to the drawing in particular the invention embodied therein comprises an anesthetic reservoir 1 having vaporizer block 2 in an upper portion thereof and having an inlet conduit 6 in an overflow conduit 9 extending into the lower portion portion of the tank 1 slanted downwardly toward a bottom 7.

The single drawing shows a partial section of an anesthetic vaporizer block 2 marked with cross-hatching. The dispensed anesthetic concentration can be adjusted in the usual manner with a hand wheel 3. A feeding tank 4 is attached to the outer wall of the anesthetic reservoir 1 through a reservoir inlet 5 via pipe length 6 and its opening 8 slanted toward but is spaced above a reservoir bottom 7. Pipe length 9, with its opening 10 also extends obliquely downwardly toward but spaced above the bottom 7 and it is connected with overflow section 11 located in the feeding tank 4. The openings 8 and 10 are close to a remote wall 1a of the reservoir 1 to an inlet section 5 and the overflow section 11. Both pipe lengths 6 and 9 are attached to a holder 12 mounted on the bottom 7.

As seen in the FIGURE, both conduits 6 and 9 are almost horizontal with their slant being rather shallow. The slant of conduit 9 is somewhat greater than the slant of inlet conduit 6 and the opening 10 of overflow conduit 9 is slightly above the opening 9 of inlet conduit 6.

While a specific embodiment of the invention has been shown and described in detail to illustrate the application of the principles of the invention, it will be understood that the invention may be embodied otherwise without departing from such principles.

What is claimed is:

1. An overflow trap for a reservoir for having liquid anesthetics therein, comprising an anesthetic tank having a bottom and opposite side walls, an anesthetic inlet conduit extending into said tank and sloping downwardly toward the bottom of said tank, and an anesthetic overflow conduit extending into said tank and sloping downwardly to an inlet opening within the tank which is at a lower level from the remaining portion of said overflow conduit, said inlet conduit ending at an opening, said openings of said inlet and overflow conduits being spaced above the bottom of said tank, each of said inlet and overflow conduits extending from the same one of said opposite side walls almost to the other of said opposite side walls, the slant of each of said inlet and overflow conduits being slight between said opposite side walls.

2. An overflow trap according to claim 1 wherein said overflow conduit slopes to a greater extent than said inlet conduit, said opening of said overflow conduit being spaced slightly above said opening of said inlet conduit.

3. A device for handling liquid anesthetics, said device including a reservoir for having liquid anesthetics therein, said reservoir including an upper chamber, said upper chamber containing an anesthetic block, said device comprising an anesthetic tank having a bottom and opposite side walls, an anesthetic inlet conduit extending into said tank and sloping downwardly toward the bottom of said tank, and an anesthetic overflow conduit extending into said tank and sloping downwardly to an inlet opening within the tank which is at a lower level from the remaining portion of said overflow conduit, said inlet conduit ending at an opening, said openings of said inlet and overflow conduits being spaced above the bottom of said tank, each of said inlet and overflow conduits extending from the same one of said opposite side walls almost to the other of said opposite side walls, the slant of each of said inlet and overflow conduits being slight between said opposite side walls, said overflow conduit slopes to a greater extent than said inlet conduit, said opening of said overflow conduit being spaced slightly above said opening of said inlet conduit, said device including a feed tank adjacent said anesthetic tank, said anesthetic inlet conduit and said overflow conduit having a portion extending into said feed tank.

4. A device according to claim 6, wherein said inlet conduit and said overflow conduit have lower portions bent at an angle from the remaining portion having said respective openings at the bottom thereof.

* * * * *